United States Patent [19]

Sasaki et al.

[11] 4,454,315

[45] Jun. 12, 1984

[54] CARBOXYMETHYLATED DERIVATIVES OF β-1,3-GLUCAN

[75] Inventors: Takuma Sasaki, Tokyo; Yukio Sugino, Toyonaka, both of Japan

[73] Assignee: Takeda Chemical Industries, Ltd., Osaka, Japan

[21] Appl. No.: 224,890

[22] Filed: Jan. 14, 1981

Related U.S. Application Data

[63] Continuation of Ser. No. 015,898, Feb. 28, 1979, abandoned, which is a continuation of Ser. No. 850,019, Nov. 9, 1977, abandoned.

[30] Foreign Application Priority Data

Nov. 18, 1976 [JP] Japan .................................. 51-139143

[51] Int. Cl.$^3$ ...................... A61K 31/715; C08B 37/00
[52] U.S. Cl. ..................................... 536/18.2; 424/180; 424/181; 536/1.1; 536/4.1; 536/115; 536/119; 536/120; 536/123
[58] Field of Search ..................... 424/181, 180; 536/1, 536/120, 115, 119, 4.1, 18.2, 1.1, 123

[56] References Cited

U.S. PATENT DOCUMENTS

| | | | |
|---|---|---|---|
| 3,301,848 | 1/1967 | Halleck | 536/1 |
| 3,396,082 | 8/1968 | Davis et al. | 536/1 |
| 3,754,925 | 8/1973 | Kimura et al. | 536/1 |
| 3,822,250 | 7/1974 | Kimura et al. | 536/1 |
| 3,856,775 | 12/1974 | Fukuoka et al. | 536/1 |

Primary Examiner—Johnnie R. Brown
Attorney, Agent, or Firm—Burgess, Ryan and Wayne

[57] ABSTRACT

It has been found that water-insoluble, thermogelable β-1,3-glucan produced by microorganisms, lower polymers obtainable upon partial hydrolysis of the glucan or, carboxymethylated derivatives of said glucan or of said lower polymers are useful for inhibiting growth of tumors in a warm-blooded animal. The inhibitory activity against various tumors of these polysaccharides is very strong and significant whenever administered to warm-blooded animals from the early to very late stage of tumor progression or even when administered prior to plantation of tumors. The carboxymethylated derivatives above-mentioned are novel water-soluble compounds which can be produced by carboxymethylation of said glucan and partial hydrolyzate thereof.

Figure 1:
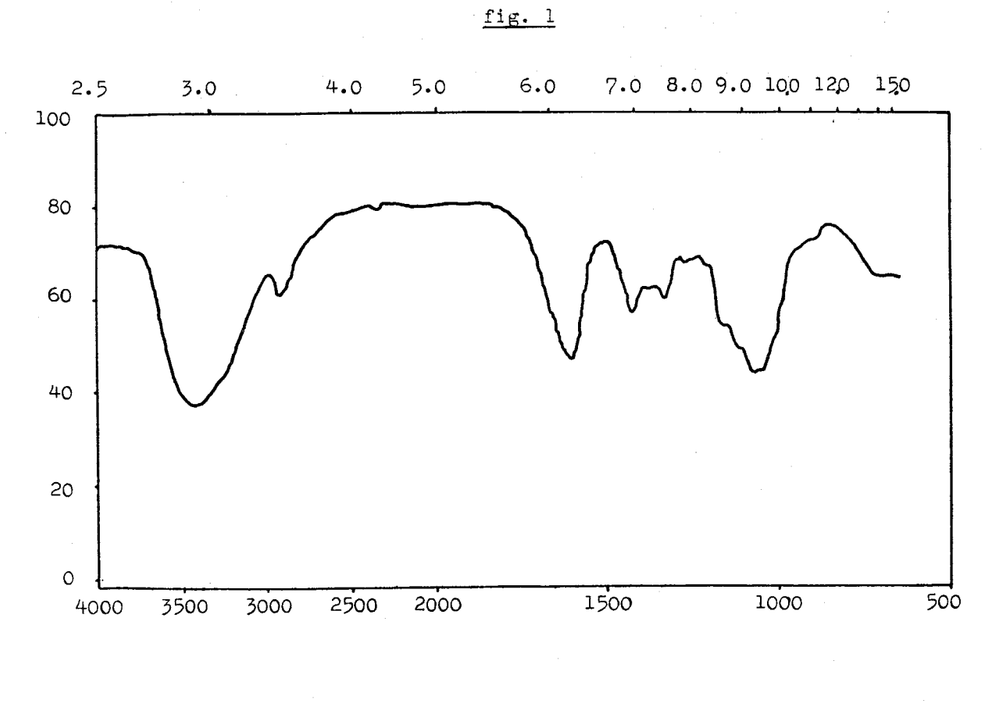
Figure 2:
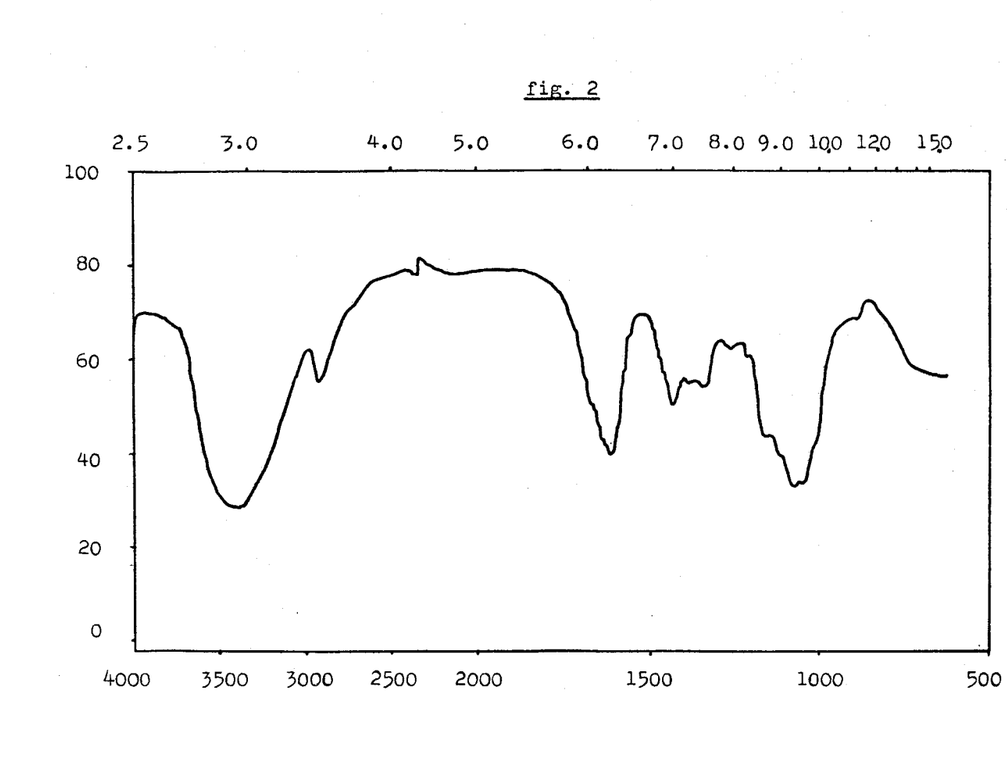

6 Claims, 2 Drawing Figures fig. 1 fig. 2

CARBOXYMETHYLATED DERIVATIVES OF β-1,3-GLUCAN

This application is a continuation of co-pending application Ser. No. 015,898, filed Feb. 28, 1979, which is a continuation of application Ser. No. 850,019, filed Nov. 9, 1977, both of which are now abandoned.

This invention relates to a treatment of tumors and a new derivative of β-1,3-glucan usable for the treatment.

For years there have been searches for substances which, with parenteral or oral administration, will cause the inhibition of tumor growth and the prolongation of the survival time of tumor-bearing warm-blooded animals without serious side effects.

It has now been found by the present inventors that a water-insoluble, thermogelable β-1,3-glucan produced by microorganisms belonging to the genus Alcaligenes and the genus Agrobacterium, partially hydrolyzed lower polymers thereof, or carboxymethylated derivatives of said glucan or of said lower polymers have a strong antitumor activity against the growth of tumors such as sarcoma, carcinoma or leukemia in a warm-blooded animal without undesirable side effects.

The principal object of the present invention is, therefore, to provide a treatment for a warm-blooded animal affected, or which may be affected, by neoplasias with the β-1,3-glucan, the lower polymers, or their carboxymethylated derivatives. And another object is to provide an antitumor agent containing the β-1,3-glucan, the lower polymers, or the carboxymethylated derivatives as active ingredients. A further object is to provide novel carboxymethylated derivatives of either the β-1,3-glucan or the lower polymers obtainable by partial hydrolysis of the β-1,3-glucan.

It is already known from Japanese Patent Publications No. 32673/1973 and No. 32674/1973 and British Pat. No. 1352938 that certain strains of microorganisms belonging to the genus Alcaligenes and the genus Agrobacterium produce a water-insoluble, thermogelable β-1,3-glucan (hereinafter referred to briefly as TAK-N). However, no pharmaceutical usage of the glucan has been known at all.

The extensive studies made by us on TAK-N, lower polymers obtainable by partial hydrolysis thereof (hereinafter referred to as TAK-D) and carboxymethylated derivatives of TAK-N or of said lower polymers (hereinafter referred to as CMTAK) led to the finding that these substances possess a strong antitumor activity giving a markedly high tumor inhibition ratio and a complete regression of tumors. The finding was followed by further studies which have resulted in the completion of this invention.

This invention is directed to a method of inhibiting the growth of a tumor in a warm-blooded animal which comprises administering to said animal to inhibit the growth of said tumor a sufficient amount of a member of the group consisting of a β-1,3-glucan which is water-insoluble and thermogelable in the presence of water at an average degree of polymerization of 170, a lower polymer obtainable upon partial hydrolysis of said glucan and a carboxymethylated derivative of said glucan or said lower polymer.

And another part of this invention is directed to an antitumor agent containing said glucan, said lower polymer or said carboxymethylated derivative.

TAK-N which is employable in accordance with this invention is such that, as described in detail in the aforementioned patent literatures, it is produced by the cultivation of certain microorganisms such as *Agrobacterium radiobacter* (IFO 13127, ATCC6466). *Agrobacterium radiobacter* U-19(IFO 13126, ATCC 21679, FERM P-1166) and *Alcaligenes faecalis* var. *myxogenes* NTK-u (IFO-13140, ATCC 21680, FERM-P 1168). This β-1,3-glucan contains β-1,3-bonds as its glycosidic linkages and is water-insoluble, most species of which have average degrees of polymerization (hereinafter abbreviated as $\overline{DP}$) not less than about 70 and a characteristic property such that they are gelable at $\overline{DP}$ 170 when heated, for example at about 60° C., in the presence of water.

The $\overline{DP}$ of TAK-N is variable according to the method of preparation. Thus, as determined by the method of Manners et al (Carbohydrate Research 17, 109(1971)), it is from about 70 to 1,000 and, in many cases, from 100 to 600. And, while these variants of glucan species are generally thermogelable in the presence of water, they lose gelability as their $\overline{DP}$ values are lowered. For Example, the glucan with $\overline{DP}$ of 113 is not gelable but that with 170 is gelable. We have discovered that all of TAK-N, TAK-D and CMTAK have a potent antitumor activity.

It is particularly surprising that even some species of TAK-D which may not be called polysaccharides because of their low degree of polymerization retain and display such an antitumor activity.

TAK-D is produced by partial hydrolysis of TAK-N. Among the methods of hydrolysis available for this purpose are such known methods as acid hydrolysis, alkaline hydrolysis and enzymatic hydrolysis with β-1,3-glucanase.

TAK-D can be separated from the reaction mixture by various procedures that are commonly practised for the purification or fractionation of polysaccharides and oligosaccharides, such as precipitation under acidic conditions, precipitation by the addition of ethanol, and gel filtration. By such procedures, various lower polymers each having the desired $\overline{DP}$ value can be obtained separately.

The term TAK-D used throughout this specification means any and all types of lower polymers which are obtainable by partial hydrolysis of TAK-N.

As aforesaid, $\overline{DP}$ of TAK-N as obtained from cultures of the aforementioned microorganisms are broadly dispersed. And since the degree of polymerization of the β-1,3-glucan produced in the course of the fermentation process tends to decrease as the cultivation time is prolonged, it is even possible to produce TAK-N with $\overline{DP}$ lower than the above-mentioned range.

On the other hand, since TAK-D is produced by the hydrolysis of TAK-N, its $\overline{DP}$ is naturally lower than the starting material TAK-N. But, generally speaking, TAK-N having degrees of polymerization corresponding to those of a large majority of TAK-D species can be produced by the cultivation of said microorganisms. And so long as TAK-N and TAK-D have the same $\overline{DP}$, no substantial difference in antitumor activity and thermogelability has been found between them.

The manner of production of TAK-D from TAK-N will now be described by way of the results of our experimental production runs.

Experiment 1 (Hydrolysis with sulfuric acid)

In 6 liters of 4N-sulfuric acid was suspended 60 g of TAK-N ($\overline{DP}$: 540 as measured by the method of Manners et al. Unless otherwise specified hereinafter, all $\overline{DP}$ values indicated were measured by this method). The hydrolysis reaction was carried out at 60° C. After 30 minutes and after one hour, a 2 liter portion of the reaction mixture was taken. These portions of the reaction mixture were designated $S_1$ and $S_2$, respectively. The remainder of the reaction mixture was further incubated at 60° C. for an additional one hour to obtain another sample $S_3$. From $S_1$, $S_2$ and $S_3$, hydrolysis products were prepared by the following procedure. First, each sample was centrifuged and the precipitate was collected. Each precipitate was then washed with 1.6 liters of distilled water and centrifuged. This procedure was repeated again and the precipitate was suspended in 1.2 liters of distilled water. The suspension was neutralized with an 8N-solution of sodium hydroxide and lyophilized. The above procedure provided 22 g, 20 g and 19 g of powders, from $S_1$, $S_2$ and $S_3$, respectively. Then 7 g portions of these powders were respectively suspended in 700 ml of distilled water and the pH was adjusted to 12.5 with an 8N solution of sodium hydroxide to yield $S_1'$, $S_2'$ and $S_3'$, respectively.

Ethanol was added to each solution to give a final concentration of 60% and, after the resulting precipitate was removed by centrifugation, ethanol was further added to the supernatant to give a concentration of 70%. Then, the solution was neutralized with dilute hydrochloric acid. The resulting precipitate was collected by centrifugation, washed 4 times with 250 ml portions of distilled water and, then, lyophilized.

In this manner, 1.8 g and 1.5 g of white powders (S-I and S-II) were obtained from $S_1'$ and $S_2'$, respectively. To $S_3'$ was added a sufficient amount of ethanol to give a final concentration of 70% and the mixture was centrifuged. The precipitate was resuspended in about 500 ml of distilled water and, after the addition of ethanol to give a concentration of 70%, the suspension was neutralized with a small amount of hydrochloric acid. The resulting precipitate was collected by centrifugation, washed 4 times with 250 ml portions of distilled water and lyophilized, which provided 5.6 g of white powder (S-III).

The physicochemical properties of S-I, S-II and S-III are shown in Table 1.

TABLE 1

|  |  | S-I | S-II | S-III |
|---|---|---|---|---|
| DP* |  | 125 | 82 | 68 |
| Elemental analysis | C | 40.13 | 40.65 | 40.94 |
| (%) | H | 6.74 | 6.77 | 6.76 |
| Purity (%)** |  | 93.1 | 91.1 | 93.8 |
| Glucose content |  | <0.1 | <0.1 | <0.1 |
| (%)*** |  | 25.6 | 19.5 | 18.8 |
| $(\alpha)_D^{25}$ in 0.1 N NaOH |  | (C = 1.16) | (C = 1.10) | (C = 0.82) |

*Measured by the method of Manners et al
**Calculated from glucose content determined by the phenol sulfuric acid method
***Measured by gas chromatography Experiment 2 (hydrolysis with formic acid)

(I) In 150 ml of 85% formic acid was dissolved 6 g of TAK-N ($\overline{DP}$: 540) and the hydrolysis reaction was carried out at 88° C. for 20 minutes. After cooling, the reaction mixture was concentrated to dryness and the concentrate was suspended in water. The suspension was brought to pH 12.5 with a 5N-solution of sodium hydroxide to obtain a clear solution. The solution was brought to pH 7.0 with 5N-hydrochloric acid and the resulting precipitate was collected by centrifugation. The precipitate was washed well with distilled water and lyophilized. By the above procedure was obtained 5.4 g of white powder (F-I).

(II) Twelve grams of the same TAK-N as used in (I) was hydrolyzed in 300 ml of 90% formic acid at 95° C. for 20 minutes and the reaction mixture was treated in essentially the same manner as in (I) to obtain 10.3 g of white powder (F-II).

(III) Twelve grams of the same TAK-N as used in (I) was hydrolysed in 300 ml of 90% formic acid at 95° C. for 40 minutes and the reaction mixture was treated in essentially the same manner as in (I) to obtain 5.4 g of white powder. The powder was dissolved in a 0.05N-aqueous solution of sodium hydroxide to give a final concentration of 1.0% and ethanol was further added to the solution to give a concentration of 57.5%. The resulting precipitate was collected by centrifugation, suspended in distilled water and neutralized with dilute hydrochloric acid. The suspension was centrifuged and the precipitate was washed well with 70% aqueous ethanol and lyophilized to obtain 2.2 g of white powder (F-V).

To the supernatant obtained upon recovery of the above ethanolic precipitate was added ethanol to give a concentration of 70% and the mixture was neutralized with hydrochloric acid. The resulting precipitate was collected by centrifugation, washed with 70% aqueous ethanol and lyophilized. By the above procedure was obtained 2.3 g of white powder (F-III). The supernatant remaining after recovery of the first precipitate (5.4 g) from the hydrolysate mixture contained a substantial amount of partial hydrolysate in a solubilized state. Therefore, this supernatant solution was concentrated and centrifuged to separate the generated precipitate. The precipitate was lyophilized to recover 2.9 g of white powder (F-VII). The resulting supernatant solution was further fractionated by gel filtration chromatography on a column of Sephadex G-25 (solvent: 0.1M ammonium bicarbonate) followed by lyophilization of combined fractions. By this procedure was obtained 0.7 g of white powder (F-VIII).

(IV) The same TAK-N (18 g) as that used in (I) was hydrolyzed in 450 ml of 90% formic acid at 95° C. for 40 minutes and, to this reaction mixture, essentially the same fractionation procedure as in (III) was applied, such as concentration, precipitation with ethanol, gel filtration, etc. By the above procedure, four fractions of white powder (F-IV, 2.3 g, F-VI 2.8 g, etc.) were obtained.

The physicochemical properties of these powders—F-I, F-II, F-III, F-IV, F-V, F-VI, F-VII and F-VIII—are shown in Table 2. When six samples having lower $\overline{DP}$ (F-III, IV, V, VI, VII, VIII) were each dissolved in a 0.02N-solution of sodium hydroxide and, chromatographed respectively on the same Sephadex G-200 column equilibrated with the same solution as above, they were eluted in the order of decreasing $\overline{DP}$ (from F-III to F-VIII), each sample giving a symmetrical peak, which indicated that each sample had a normal distribution in regard to degree of polymerization.

TABLE 2

|  | DP* | Elemental analysis (%) C | Elemental analysis (%) H | Purity (%)** | Glucose Content (%)*** | $[\alpha]_D^{25}$ in 0.1 N NaOH |
|---|---|---|---|---|---|---|
| F-I | 299 | 40.75 | 6.46 | 92.3 | <0.03 | 30.6(C = 0.35) |
| F-II | 113 | 41.71 | 6.91 | 98.4 | <0.03 | 22.3(C = 0.57) |
| F-III | 50 | 41.98 | 6.77 | 93.5 | <0.03 | 12.1(C = 1.06) |
| F-IV | 44 | 42.35 | 6.50 | 90.8 | <0.03 | 10.9(C = 2.24) |

TABLE 2-continued

| | DP* | Elemental analysis (%) C | H | Purity (%)** | Glucose Content (%)*** | $[\alpha]_D^{25}$ in 0.1 N NaOH |
|---|---|---|---|---|---|---|
| F-V | 39 | 41.44 | 6.71 | 93.3 | <0.03 | 4.0(C = 1.62) |
| F-VI | 24 | 42.62 | 6.99 | 92.5 | <0.03 | −1.5(C = 1.07) |
| F-VII | 16 | 42.46 | 6.99 | 91.8 | <0.03 | 0.4(C = 1.06) |
| F-VIII | 7 | 39.84 | 6.37 | 94.1 | <0.03 | 0.0(C = 0.57) |

*,  and *: see the footnote to TABLE 1

We have also discovered that the carboxymethylation of TAK-N and TAK-D yields new derivatives (CMTAK) in which hydroxyl groups of these glucans are more or less carboxymethylated.

Some aspects of this invention are predicated upon the above finding. Thus, the invention is also directed to β-1,3-glucan derivatives of the following general formula and their salts.

(I)

(wherein at least one of R's is —CH$_2$COOH, with the remainder, if any, being H; n is an integer.) CMTAK is produced by carboxymethylating β-1,3-glucan or its hydrolysate of the formula:

wherein n is an integral number, and whose $\overline{DP}$ is between 2 and 1000.

CMTAK can be obtained by carboxymethylating TAK-N or TAK-D in a known manner, for example by reacting TAK-N or TAK-D with monochloroacetic acid in the presence of alkali. In addition to this method, any other conventional methods that are used for the carboxymethylation of carbohydrates may be employed.

To recover CMTAK from the reaction mixture, it is possible to employ conventional methods that are commonly used for the purification of carbohydrates, such as precipitation by the addition of an organic solvent. In addition, such other procedures as ion exchange chromatography, gel filtration, etc. may likewise be utilized according to the content of carboxymethyl groups in, or the solubility in water of, CMTAK.

While the CMTAK thus obtained contains carboxymethyl groups in its molecule, the content of carboxymethyl groups varies widely depending upon the conditions of the carboxymethylation reaction. As determined by titration, the content of carboxymethyl groups of the CMTAK obtained by a normal carboxymethylation reaction procedure is generally less than 3 carboxymethyl groups per glucose residue in the CMTAK molecule. CMTAK, as it is suitable for the purposes of this invention, includes all substances which are obtainable by the carboxymethylation of TAK-N or TAK-D and the molecules of which contain detectable carboxymethyl groups, irrespective of the degree of carboxymethylation.

As will be apparent from the general formula (I) given hereinbefore as its free acid, CMTAK can react with various bases to form the corresponding salts, such as the sodium, potassium, calcium, aluminum, magnesium and amine salts. In the context of this invention, CMTAK includes not only its free acid but also its salts, particularly those with low toxicity.

Table 3 shows the physical properties of some representative species of CMTAK which we prepared from TAK-N and TAK-D by the procedure described hereinbefore. The determinations of such physical properties were also made after each sample was previously dried under reduced pressure and over phosphorus pentoxide at 60° C. for 10 hours.

TABLE 3

| CMTAK No. | Example No.* | Starting Material Type | DP* | —CH$_2$COOH content*** | Elemental Analysis (%) C | H | Na | Viscosity (centipoise)**** | $[\alpha]_D^{25}$ in 0.1 N NaOH |
|---|---|---|---|---|---|---|---|---|---|
| 1 | 13 | TAK-N | 540 | 0.54 | 40.97 | 5.57 | 2.7 | 2.57 | 6.0 (C = 0.77) |
| 2 | 14 | " | 540 | 0.75 | 38.51 | 5.45 | 5.7 | 2.71 | 10.1 (C = 0.76) |
| 3 | 15 | " | 540 | 1.07 | 37.89 | 4.77 | 10.0 | 2.60 | 3.7 (C = 0.79) |
| 4 | 16 | " | 255 | 0.30 | 40.82 | 6.05 | 2.7 | 2.10 | 15.1 (C = 0.80) |
| 5 | 17 | " | 255 | 0.36 | 39.82 | 6.06 | 3.9 | 2.27 | 10.0 (C = 0.74) |
| 6 | 18 | TAK-D | 299 | 0.59 | 38.84 | 5.71 | 4.8 | 2.25 | 14.6 (C = 0.82) |
| 7 | 18 | " | 299 | 1.15 | 37.93 | 4.86 | 9.0 | 2.29 | 1.5 (C = 0.81) |
| 8 | 19 | " | 113 | 0.51 | 40.22 | 5.74 | 4.7 | 1.96 | 12.2 (C = 0.71) |
| 9 | 20 | " | 113 | 1.22 | 37.03 | 4.78 | 9.9 | 1.49 | 3.1 (C = 0.78) |
| 10 | 19 | " | 68 | 0.36 | 40.46 | 5.96 | 3.5 | 1.68 | 10.0 (C = 0.74) |
| 11 | 20 | " | 68 | 0.45 | 39.41 | 5.93 | 4.6 | 1.83 | 9.5(C = 0.78) |

*The numbers of the Examples in which the CMTAK is produced.
**Determined by the method of Manners et al.
***The number of carboxymethyl groups per glucose residue.
****Determined by a coaxial rotating viscometer under the following conditions. Solvent, a 0.1 N— solution of sodium hydroxide; concentration, 0.2 %; temperature, 30° C.; shear rate, 1046.7(sec.$^{-1}$)

FIGS. 1 and 2 show the I.R. spectra in potassium bromide of CMTAK No. 2 and No. 11 in Table 3, respectively. Numerals at the topside, the left side and the bottom side of each of the figs. indicate wavelength($\mu$), transmittance(%) and wave number(cm$^{-1}$), respectively.

The characteristic absorptions were found at 1440–1400 and 891 cm$^{-1}$.

The TAK-N, TAK-D and CMTAK obtained as above, ranging from 2 to about 1,000, preferably from 15 to 800, more preferably from 40 to 600 in $\overline{DP}$, possess a significant inhibitory activity against various kinds of tumors in warm-blooded animals including domestic animals, poultry, dogs, cats, rabbits, rats, mice, etc., and particularly against solid tumors which are known to be less sensitive to treatments with generally known cytotoxic antitumor drugs.

For instance, the growth of sarcoma 180, Ehrlich carcinoma, SN-36 leukemia, CCM adenocarcinoma, or NTF reticulum cell sarcoma each transplanted subcutaneously into mice was markedly inhibited when TAK-N, TAK-D or CMTAK was administered intraperitoneally, intravenously or subcutaneously, before, after or at the time of transplantation, once or repeatedly at dose levels of about 1 to 1,000 mg/kg per administration per day.

The toxicities of TAK-N, TAK-D and CMTAK are extremely low. For example, no toxic effect was observed both in mice and rats at a dose of 3,000 mg/kg by intraperitoneal route or 10,000 mg/kg by oral route. Thus, these polysaccharides can be safely administered to warm-blooded animals repeatedly.

The administration may be accomplished by general procedures which are normally applied in the management of cancers. Thus, intra-tumor, subcutaneous, intramuscular, or intravenous injections, if necessary, oral and rectal administrations, or in external applications, coating, instillation and other methods of administration are feasible.

According to the present invention, TAK-N, TAK-D or CMTAK is administered in a sufficient amount to a warm-blooded animal to inhibit growth of its tumor.

The dosage and procedure of the administration of TAK-N, TAK-D or CMTAK to the warm-blooded animal affected by neoplasias may vary according to the kind of agents (TAK-N, TAK-D, CMTAK), animals, tumorous symptoms, administration forms and other factors. Generally, the sufficient amount of dosage per administration is about 0.02 to 2,000 mg/kg body weight, preferably 0.2 to 2,000 mg/kg body weight, the preferred upper limit being about 500 mg/kg body weight. In many cases, about 200 mg/kg is the most desirable upper limit.

The administration may be conducted, for example, one to six times per day for consecutive or intermittent days.

The form of injection is varied in each case but can be realized in a per se conventional manner, that is to say, TAK-N, TAK-D or CMTAK is dissolved or suspended in an aqueous liquid medium directly or with a conventional solubilizer such as alcohols (e.g. ethanol, propyleneglycol), non-ionic surface active agents, physiological saline and isotonic solutions. In the case of CMTAK, the sample is easily dissolved in distilled water or physiological saline.

For oral preparation, any member of pharmaceutical forms can be used, for example, syrups, elixirs, suspensions or the compound can be processed into wafers, pills, tablets suppositories, gel and the like. In a preferred embodiment, the oral dosage form consists of a tablet containing between about 10 and 1,000 mg of the above active ingredient per tablet. Such tablets can be coated in the usual fashion, preferably using a readily soluble coating material, for example, sugar, etc. The above amount can also be incorporated into gelatin capsules which promptly dissolve upon introduction into the stomach. In any event, the usual flavoring and coloring agents can be used without effect on the active ingredient so incorporated.

Tablets of this type are prepared in the usual fashion by compounding the active ingredient with a binding agent, e.g., starch, sugar and the like, granulating the mixture and, after adding the necessary fillers, flavoring agents, lubricants, etc., the mixture is slugged and passed through a 30-mesh screen. The thoroughly blended mixture is then compressed into tablets of desired hardness with the usual punch, preferably to make bisected tablets for easier administration.

TAK-N, TAK-D and CMTAK may be administered in combination with other antitumor agents. Combination with the other antitumor agents leading to enhanced immunological activity of the tumor-bearing animals is also desirable.

The invention will be further described by way of examples. Some of these examples show the process of production of TAK-D from TAK-N, the process of production of CMTAK, the physical properties of TAK-N, TAK-D and CMTAK, and some of the injectable forms of these agents. Other examples demonstrate the antitumor activities of TAK-N, TAK-D and CMTAK against mouse tumors by way of models.

As demonstrated above, the treatment of a tumor-bearing animal with the compounds produces drastic regression of various kinds of tumors such as sarcoma, carcinoma, reticulum cell sarcoma and leukemia. All of these types of tumors in rodents have been known to be reliable models for tumors in other warm-blooded animals.

It should, of course, be understood that these examples are by no means limitative of this invention.

Most of the following experiments on antitumor activity of TAK-N, TAK-D, and CMTAK were tested by approximately the same methods as those described for antitumor activity of lentinan, a branched glucan from an edible mushroom, by Chihara, G. et al. (See Nature 222, 687–688, 1969, and Cancer Research 30, 2776–2781, 1970).

Mouse tumors used in the experiments such as sarcoma 180 (S180), Ehrlich carcinoma (Ehrlich), NTF reticulum cell sarcoma (NTF), CCM adenocarcinoma (CCM) and leukemia SN-36(SN-36) were maintained in ICR-JCL mice, 5 to 7 weeks old, each in an ascites form. A suitable number of these tumor cells was subcutaneously transplanted into ICR-JCL mice, and the tumor nodes which had grown up were excised for weighing on the 35th day after the tumor transplantation.

A TAK-N or TAK-D, was suspended or dissolved in distilled water or in physiological saline, and CMTAK was dissolved in distilled water or in physiological saline in adequate concentrations and at around neutral pH values. Each preparation was administered intraperitoneally, subcutaneously or intravenously to mice (0.2 ml/20 g body weight) daily for 10 days starting at 24 hours after the tumor transplantation, daily for 5 days before tumor transplantation, or only once during the 7th day before and the 21st day after the tumor implantation.

EXAMPLE 1

Tumor Suppressive Effect of TAK-N (DP 540): Single Injection

Four millions of S 180 cells were subcutaneously transplanted into the left inguinal region of ICR-JCL female mice, 4 to 5 weeks old. The tumor nodes were excised on the 35th day after the transplantation, and weighed. The average tumor weight of a treated group (T) consisting of 5 mice was compared with that of control group (C) consisting of 10 mice, and the tumor inhibition ratio (% Inhibition: (C-T)/C×100) was calculated. The number of tumor-free animals (complete regression) on the 35th day was also counted.

TAK-N (DP 540) suspended in physiological saline (10 mg/ml) was administered intraperitoneally (0.2 ml/20 g body weight) once to each animal at the dose level of 100 mg/kg on the 7th, 3rd or 1st day before, or the 1st, 2nd, 3rd, 5th, 7th, 10th, 14th, or 21st day after the tumor transplantation, or on the day of tumor transplantation.

As shown in Table 4, TAK-N at the dose level of 100 mg/kg inhibited the growth of S 180 significantly when the test sample was administered only once during the 7th day before and the 21st day after the tumor transplantation.

In addition, by a single administration of TAK-N (DP 540) on the 7th day after the tumor transplantation at the dose levels of 20 mg/kg, 60 mg/kg and 100 mg/kg, a significant suppression of the tumor growth was observed at two higher doses, 60 mg/kg and 100 mg/kg.

TABLE 4

| Sample | Dose mg/kg (ip) | Day of injection | Average tumor weight (g) | Tumor inhibition ratio (%) | No. of complete regression/No. of treated mice |
|---|---|---|---|---|---|
| | — | | 7.06 | — | 0/10 |
| TAK-N (DP 540) | 100 × 1 | −7* | 2.27 | 67.8 | 3/5 |
| | 100 × 1 | −3 | 1.64 | 76.8 | 3/5 |
| | 100 × 1 | −1 | 0 | 100 | 5/5 |
| | 100 × 1 | 0** | 0.56 | 92.1 | 3/5 |
| | — | | 6.94 | — | 0/10 |
| TAK-N (DP 540) | 100 × 1 | 1*** | 1.19 | 82.9 | 4/5 |
| | 100 × 1 | 2 | 0.59 | 91.5 | 4/5 |
| | 100 × 1 | 3 | 0 | 100 | 5/5 |
| | 100 × 1 | 5 | 1.25 | 82.0 | 3/5 |
| | 100 × 1 | 7 | 0 | 100 | 5/5 |
| | — | | 5.08 | — | 0/10 |
| TAK-N (DP 540) | 100 × 1 | 7 | 0 | 100 | 5/5 |
| | 100 × 1 | 10 | 0.01 | 99.8 | 4/5 |
| | 100 × 1 | 14 | 0.01 | 99.8 | 4/5 |
| | 100 × 1 | 21 | 1.71 | 66.3 | 1/5 |
| | — | | 5.36 | — | 0/5 |
| TAK-N (DP 540) | 20 × 1 | 7 | 3.72 | 30.6 | 1/5 |
| | 60 × 1 | 7 | 0.12 | 97.8 | 3/5 |
| | 100 × 1 | 7 | 0.03 | 99.4 | 4/5 |

*TAK-N was administered on the 7th day before the tumor transplantation
**TAK-N was administered on the 1st day after the tumor transplantation
***TAK-N was administered on the day of tumor transplantation These results indicate that TAK-N (DP 540) is effective in suppressing the tumor growth at all stages of tumor progression in warm-blooded animals even by a single administration.

EXAMPLE 2

Tumor Suppressive Effect of TAK-N (DP 540) and Autoclave-curdled TAK-N (DP 540):

Six millions of S 180 cells were subcutaneously transplanted into the right inguinal region of ICR-JCL mice with body weights of about 23 g. The tumor nodes were excised on the 35th day after the transplantation, and weighed. The tumor inhibition ratio in a treated group was calculated as in Example 1.

TAK-N (DP 540) and autoclave-curdled TAK-N (DP 540) were used. The latter was obtained by heating a 2% suspension of TAK-N (DP 540) at 120° for 25 minutes followed by drying and powdering the formed gel. The samples were suspended in distilled water at desired concentrations, and each suspension was administered intraperitoneally to a group of 5 mice daily for 10 days starting at 24 hours after the tumor transplantation.

As shown in Table 5, TAK-N (DP 540) showed a pronounced effect on the growth of tumors at the dose level from 1 to 50 mg/kg, the effect being particularly significant at the dose level from 5 to 25 mg/kg.

The autoclaved TAK-N (DP 540) was also effective in tumor growth suppression at the dose level of 10 mg/kg. There was no observed toxicity.

TABLE 5

| Sample | Dose mg/kg (ip) | Average tumor weight (g) | Tumor inhibition ratio (%) | No. of complete regression/No. of treated mice |
|---|---|---|---|---|
| | — | 6.00 | — | 0/6 |
| TAK-N (DP 540) | 1 × 10 | 4.80 | 20.0 | 0/6 |
| | 3 × 10 | 3.58 | 40.3 | 1/6 |
| | 5 × 10 | 0.02 | 99.7 | 5/6 |
| | 7 × 10 | 0.73 | 87.8 | 5/6 |
| | 10 × 10 | 0.01 | 99.8 | 5/6 |
| | 15 × 10 | 0.10 | 98.3 | 4/5 |
| | 20 × 10 | 0 | 100 | 5/5 |
| | 25 × 10 | 0.42 | 93.0 | 3/6 |
| | 50 × 10 | 1.19 | 80.2 | 1/6 |
| TAK-N (Dp 540) gel* | — | 3.67 | — | 0/6 |
| | 10 × 10 | 0.29 | 92.1 | 5/6 |

*Autoclave-treated

These results indicate that TAK-N is useful in tumor retardation at relatively low dose levels and that the sample can be sterilized by autoclaving without loss of its activity.

EXAMPLE 3

Tumor Inhibitory Activity of Various Kinds of TAK-N and TAK-D

From 24 hours after the transplantation of S180 as described in Example 2, various kinds of TAK-N and TAK-D suspended in distilled water were administered intraperitoneally at the dose level of 10 mg/kg to a group of 5 mice daily for 10 days. The tumor nodes were excised on the 35th day after the tumor transplantation, and weighed. The inhibition ratios were calculated as in Example 1.

As shown in Table 6, all samples used exhibited an inhibitory activity against the tumor growth. Especially, those samples having $\overline{DP}$ over 50 showed a strong antitumor activity with many complete regression.

TABLE 6

| Sample | | Dose mg/kg (ip) | Average tumor weight (g) | Tumor inhibition ratio (%) | No. of complete regression/No. of treated mice |
|---|---|---|---|---|---|
| | | — | 5.46 | — | 0/6 |
| TAK-N | ($\overline{DP}$ 565) | 10 × 10 | 0.07 | 98.7 | 5/6 |
| | ($\overline{DP}$ 540) | " | 0.20 | 96.3 | 3/5 |
| | ($\overline{DP}$ 380) | " | 0.46 | 91.6 | 4/6 |
| | ($\overline{DP}$ 125) | " | 0 | 100 | 6/6 |
| | | — | 5.46 | — | 0/6 |
| TAK-D | S-II ($\overline{DP}$ 82) | 10 × 10 | 0 | 100 | 6/6 |
| | S-III ($\overline{DP}$ 68) | " | 0.03 | 99.5 | 5/6 |
| | F-III ($\overline{DP}$ 50) | " | 0 | 100 | 6/6 |
| | F-V ($\overline{DP}$ 39) | " | 2.03 | 62.8 | 1/6 |
| | F-VI ($\overline{DP}$ 24) | " | 3.60 | 34.1 | 0/6 |
| | F-VII ($\overline{DP}$ 16) | " | 1.54 | 71.8 | 1/6 |

These results indicate that both TAK-N and TAK-D are effective in tumor growth regression irrespective of their $\overline{DP}$ values.

EXAMPLE 4

Tumor Suppressive Effects of CMTAK and Autoclave-treated CMTAK

The antitumor activity of three kinds of CMTAK prepared from TAK-N ($\overline{DP}$ 540) (CMTAK Nos. 1, 4, 5) and of autoclaved CMTAK was assayed as described in Example 2. Samples were dissolved in distilled water for injection, and the pH was adjusted to around 7.0. In some experiments one of these samples (CMTAK No. 1) was sterilized by autoclaving (120° C., 25 minutes) before further administration.

As shown in Table 7, all CMTAK samples at the dose level of 10 mg/kg inhibited significantly the tumor growth. These growth inhibition by CMTAK was observed at dose levels from 1 to 40 mg/kg.

TABLE 7

| Sample | Dose mg/kg. (ip) | Average tumor weight (g) | Tumor inhibition ratio (%) | No. of complete regression No. of treated mice |
|---|---|---|---|---|
| | — | 2.87 | — | 0/7 |
| CMTAK No. 1 | 10 × 9 | 0 | 100 | 7/7 |
| No. 4 | 10 × 9 | 0.28 | 90.2 | 4/7 |
| No. 5 | 10 × 9 | 0.01 | 99.7 | 6/7 |
| Autoclaved | — | 3.65 | — | 0/6 |
| CMTAK No. 1 | 1 × 10 | 0.77 | 78.9 | 1/6 |
| | 3 × 10 | 0.03 | 99.2 | 5/6 |
| | 5 × 10 | 0.23 | 93.7 | 4/6 |
| Autoclaved | — | 2.17 | — | 0/6 |
| CMTAK No. 1 | 5 × 10 | 0 | 100 | 6/6 |
| | 10 × 10 | 0.07 | 96.8 | 5/6 |
| | 15 × 10 | 0.08 | 96.3 | 5/6 |
| | 20 × 10 | 0.21 | 90.3 | 3/6 |
| | 40 × 10 | 0.18 | 91.7 | 1/6 |

These results indicate that CMTAK can be sterilized without loss of its antitumor activity and that they are useful in an injectable form for cancer treatment.

EXAMPLE 5

Tumor Suppressive Effects of TAK-N, TAK-D and CMTAK by various Routes of Administration TAK-N ($\overline{DP}$ 540), TAK-D (F-III: $\overline{DP}$ 50), TAK-D (F-VII: $\overline{DP}$ 16), and CMTAK No. 1 were administered at the dose level of 5 mg/kg intravenously, subcutaneously or intraperitoneally for 10 consecutive days to ICR-JCL mice which were previously transplanted with $4 \times 10^6$ cells at 24 hours before the first injection. The inhibition ratio of tumor growth were calculated as in Example 1.

As shown in Table 8, in each case, the significant inhibition of tumor growth was observed. By intraveous administration, TAK-N, CMTAK, and even F-VII ($\overline{DP}$ 16) inhibited the tumor growth almost completely, the inhibition ratio being over 85% with the complete tumor regression in 4 or 5 out of 5 mice treated.

TABLE 8

| Sample | Dose (mg/kg) | Route of administration | Average tumor weight (g) | Tumor inhibition ratio (%) | No. of complete regression/No. of treated mice |
|---|---|---|---|---|---|
| | — | | 7.30 | — | 0/10 |
| CMTAK No. 1 | 5 × 10 | iv | 0.84 | 87.5 | 4/5 |
| | 5 × 10 | sc | 3.77 | 48.4 | 0/5 |
| | 5 × 10 | ip | 0.91 | 88.5 | 2/5 |
| | — | | 7.30 | — | 0/10 |
| TAK-N ($\overline{DP}$ 540) | 5 × 10 | iv | 0 | 100 | 5/5 |
| | 5 × 10 | sc | 2.72 | 63 | 3/5 |
| | 5 × 10 | ip | 0.17 | 98 | 4/5 |
| TAK-D F-III ($\overline{DP}$ 50) | 5 × 10 | iv | 3.02 | 59 | 2/5 |
| | 5 × 10 | sc | 0.91 | 88 | 3/5 |
| | 5 × 10 | ip | 2.30 | 68 | 3/5 |
| TAK-D F-VII ($\overline{DP}$ 16) | 5 × 10 | iv | 1.06 | 85 | 4/5 |
| | 5 × 10 | sc | 2.67 | 63 | 3/5 |
| | 5 × 10 | ip | 2.34 | 68 | 2/5 |

These results indicate that TAK-N, CMTAK and TAK-D are effective in tumor suppression by any route of administration.

EXAMPLE 6

Tumor Suppressive Effects of TAK-N, TAK-D and CMTAK Administered Before Tumor Transplantation: Pre-treatment TAK-N, TAK-D having different average degrees of polymerization and CMTAK No. 1 were administered intraperitoneally to ICR-JCL mice with body weights of about 23 g at dose level from 3 mg/kg to 80 mg/kg daily for 5 consecutive days. TAK-N and TAK-D were suspended, and CMTAK was dissolved, in distilled water. In the case of CMTAK the final pH was adjusted to around 7.0. Then, on the 1st or 3rd day after the last administration, $6 \times 10^6$ cells of S180 were transplanted subcutaneously into the right inguinal region of each animal. On the 35th day after the transplantation, the tumor nodes were excised and weighed. Tumor inhibition ratios were calculated as in Example 1.

As shown in Table 9, a marked growth inhibition was observed by each sample. Especially TAK-N ($\overline{DP}$ 540), CMTAK and TAK-D having $\overline{DP}$ over 50 exhibited a strong inhibitory activity. CMTAK was effective for tumor retardation at dose level as low as 3 mg/kg.

These results indicate that the polysaccharides mentioned above are useful as prophylactics in cancer treatment.

EXAMPLE 7

Tumor Suppressive Activity of TAK-N and CMTAK against Various Kinds of Tumors

Ehrlich carcinoma, CCM adenocarcinoma, NTF reticulum cell sarcoma and SN-36 leukemia were used to examine the usefulness of TAK-N and CMTAK for the retardation of various kinds of tumors.

ICR-JCL mice with an average body weight of 23 g were transplanted subcutaneously with $3.1 \times 10^6$ Ehrlich cells, $1.1 \times 10^7$ CCM cells, $4.5 \times 10^6$ NTF cells or $7.2 \times 10^4$ SN-36 cells and were administered intraperitoneally with TAK-N ($\overline{DP}$ 540) suspended in distilled water or CMTAK No. 1 dissolved in distilled water (pH 7.0) and autoclaved, at dose levels from 10 to 50 mg/kg daily for 10 days starting at 24 hours after the transplantation. The tumors were excised and weighed 35 days after the transplantation and the inhibition ratios of tumors in the treated groups were calculated as in Example 1.

TABLE 9

| Sample | Dose mg/kg (ip) | Day of injection | Average tumor weight (g) | Tumor inhibition ratio (%) | No. of complete regression/No. of treated mice |
|---|---|---|---|---|---|
| | — | | 5.06 | — | 0/5 |
| TAK-N ($\overline{DP}$ 540) | 20 × 5 | −5 to −1 | 0.37 | 92.7 | 4/6 |
| TAK-N ($\overline{DP}$ 125) | 20 × 5 | −5 to −1 | 0.98 | 80.6 | 2/6 |
| | — | | 10.10 | — | 0/6 |
| S-II ($\overline{DP}$ 82) | 20 × 5 | −5 to −1 | 0.20 | 98.0 | 4/5 |
| S-III ($\overline{DP}$ 68) | 20 × 5 | −5 to −1 | 0.35 | 96.5 | 5/6 |
| F-III ($\overline{DP}$ 50) | 20 × 5 | −5 to −1 | 1.30 | 87.1 | 3/5 |
| F-V ($\overline{DP}$ 39) | 20 × 5 | −5 to −1 | 5.52 | 45.3 | 0/6 |
| F-VI ($\overline{DP}$ 24) | 20 × 5 | −5 to −1 | 4.18 | 58.6 | 0/6 |
| F-VII ($\overline{DP}$ 16) | 20 × 5 | −5 to −1 | 5.84 | 42.2 | 0/6 |
| | — | | 6.43 | — | 0/6 |
| CMTAK No. 1 | 3 × 5 | −5 to −1 | 1.44 | 77.6 | 3/5 |
| | 5 × 5 | −5 to −1 | 3.55 | 44.8 | 1/6 |
| | 10 × 5 | −5 to −1 | 0.19 | 97.1 | 3/6 |
| | 20 × 5 | −5 to −1 | 0.05 | 99.2 | 4/6 |
| | — | | 5.03 | — | 0/5 |
| CMTAK No. 1 | 40 × 5 | −5 to −1 | 0.11 | 97.8 | 4/6 |
| | 80 × 5 | −5 to −1 | 0.15 | 97.0 | 4/6 |
| | — | | 7.45 | — | 0/5 |
| TAK-N ($\overline{DP}$ 540) | 20 × 5 | −7 to −3 | 0.18 | 97.6 | 3/5 |
| TAK-D S-III ($\overline{DP}$ 68) | 20 × 5 | −7 to −3 | 0.75 | 89.9 | 4/5 |

As shown in Table 10, in each case, a significant inhibition of tumor growth was observed.

TABLE 10

| Tumor | Sample | Dose mg/kg (ip) | Average tumor weight (g) | Tumor inhibition ratio (%) | No. of complete regression/No. of treated mice |
|---|---|---|---|---|---|
| Ehrlich carcinoma | TAK-N ($\overline{DP}$ 540) | — | 3.54 | — | 0/5 |
| | | 10 × 10 | 2.37 | 33.1 | 0/5 |
| | | 20 × 10 | 0.50 | 85.9 | 2/6 |
| | | 40 × 10 | 0.93 | 73.7 | 0/5 |
| | CMTAK | — | 1.93 | — | 1/6 |
| | | 20 × 10 | 0.80 | 58.5 | 3/6 |

TABLE 10-continued

| Tumor | Sample | Dose mg/kg (ip) | Average tumor weight (g) | Tumor inhibition ratio (%) | No. of complete regression/No. of treated mice |
|---|---|---|---|---|---|
| | No. 1 | 40 × 10 | 0.60 | 68.9 | 2/6 |
| CCM adeno-carcinoma | TAK-N | — | 3.42 | — | 0/6 |
| | (DP 540) | 20 × 10 | 0.79 | 76.9 | 2/6 |
| | CMTAK | — | 3.42 | — | 1/6 |
| | No. 1 | 20 × 10 | 1.03 | 69.9 | 1/6 |
| | | — | 0.91 | — | 2/6 |
| Leukemia | TAK-N | 10 × 10 | 0.18 | 80.2 | 4/5 |
| SN-36 | (DP 540) | 25 × 10 | 0.19 | 79.1 | 3/5 |
| | | 50 × 10 | 0.23 | 74.7 | 2/6 |
| NTF | TAK-N | — | 7.64 | — | 0/6 |
| reticulum cell | (DP 540) | 10 × 10 | 0.38 | 95.0 | 2/6 |
| sarcoma | | 30 × 10 | 2.21 | 71.1 | 0/6 |

The results indicate that TAK-N and CMTAK have an antitumor activity against several types of tumors, i.e. sarcoma, carcinoma, adenocarcinoma, leukemia and so forth.

EXAMPLE 8

The four preparations of CMTAK (CMTAK No. 2, 6, 9 and 11) were each dissolved in physiological saline and, according to the procedure of Example 4, their effects of S180 tumor were examined. All samples, at the daily dose level of 5 mg/kg per administration for 10 days starting at 24 hours after the tumor transplantation, significantly suppressed the tumor growth.

EXAMPLE 9

| TAK-N (replaceable by TAK-D or CMTAK) | 150 mg |
|---|---|
| Lactose | 48 mg |
| Magnesium stearate | 2 mg |
| Total | 200 mg |

The above amount makes up one capsule.

TAK-N (TAK-D or CMTAK) and lactose are mixed in the aboveindicated proportions, tableted and pulverized. Then, magnesium stearate is added. The mixture is dispensed into capsules.

EXAMPLE 10

| TAK-N (replaceable by TAK-D or CMTAK) | 400 mg |
|---|---|
| Lactose | 95 mg |
| HPC-L (hydroxypropyl cellulose) | 5 mg |
| Total | 500 mg |

The above amount makes up a single dose.

The above three ingredients are mixed together in the indicated proportions and with the addition of a small amount of water, the mixture is kneaded in a kneader, granulated, dried, regranulated, size-selected and packaged in doses indicated above.

EXAMPLE 11

(a) One gram of TAK-D ($\overline{DP}$ 16) is dissolved in 1,000 ml of distilled water for injection (or is filtered and the filtrate is distributed into ampoules in 500 ml portions. After sealing, the ampoules are heat-sterilized in a routine manner.

(b) Two gram of CMTAK (the product of Example 14) is dissolved in 100 ml of distilled water for injection (or physiological saline) and the solution is filtered. The filtrate is distributed into ampoules in 20 ml portions and, after sealing by fusion, the ampoules are heat-sterilized in a routine manner.

EXAMPLE 12

| TAK-N (replaceable by TAK-D or CMTAK) | 160 mg |
|---|---|
| Sorbitol | 200 mg |
| Sodium carboxymethylcellulose | 10 mg |
| Polysorbate 80 | 3.2 mg |
| Methyl p-hydroxybenzoate | 4 mg |
| Propyl p-hydroxybenzoate | 0.4 mg |

The above ingredients are mixed in distilled water for injection to make a total volume of 4 ml. (When CMTAK is employed, the solution is neutralized, if necessary, with N/10—sodium hydroxide)

EXAMPLE 13

In 80 ml of isopropyl alcohol was suspended 3 g of TAK-N ($\overline{DP}$ 540) and the suspension was stirred at room temperature for 30 minutes. Then, 8 ml of a 30% solution of sodium hydroxide was slowly added with stirring over a period of about 60 minutes. The mixture was further stirred vigorously at room temperature for about 90 minutes for the purpose of preventing the formation of a gel. Then, 3.6 g of monochloroacetic acid was added, and the mixture was stirred at 60°–70° C. for 5 hours to allow the carboxymethylation to proceed. The product was recovered by filtration and thoroughly washed with a mixture of methanol and acetic acid (7:3, v/v). The precipitate was collected by filtration, washed well with 80% aqueous methanol, methanol and acetone in the order mentioned and dried under reduced pressure. By the above procedure was obtained 2.9 g of CMTAK. Carboxymethyl content (the number of carboxymethyl group per glucose residue; the same definition also applies hereinafter): 0.54.

EXAMPLE 14

In 40 ml of isopropyl alcohol was suspended 1.5 g of TAK-N ($\overline{DP}$ 540) and the suspension was stirred at room temperature for 30 minutes. Then, under stirring, 2 ml of a 30% solution of sodium hydroxide was added in four installments, i.e. 0.5 ml each at intervals of 15 minutes. The mixture was further stirred at room temperature for 90 minutes. Then, 0.9 g of monochloroacetic acid was added in three installments, i.e. 0.3 g each at intervals of 10 minutes. The carboxymethylation was thus conducted at 50° C. with stirring for 150 minutes. The product was collected by centrifugation, dissolved in 50 ml of water and neutralized with acetic acid. To this neutral solution was added 120 ml of methanol and the resulting precipitate was collected by centrifugation. The precipitate was washed with a mixture of 300 ml of 80% aqueous methanol and 100 ml of ethanol and, then, with a mixture of 300 ml of 80% aqueous methanol and 200 ml of ether. The product was finally lyophilized to recover 1.7 g of CMTAK. Carboxymethyl content: 0.75.

EXAMPLE 15

In 40 ml of isopropyl alcohol was suspended 1.5 g of TAK-N ($\overline{DP}$ 540) and the suspension was stirred at room temperature for 30 minutes. Then, 4 ml of a 30% solution of sodium hydroxide was added in 4 installments, 1 ml each at intervals of 15 minutes, followed by stirring at room temperature for 90 minutes. Thereafter, 1.8 g of monochloroacetic acid was added in 3 installments, i.e. 0.6 g each at intervals of 10 minutes. The mixture was stirred at 50° C. for 150 minutes, whereby the carboxymethylation was allowed to proceed. The product was collected by centrifugation, dissolved in 40 ml of water and neutralized with acetic acid. To this neutral solution was added 90 ml of methanol and the resulting precipitate was collected by centrifugation. The precipitate was washed well with a mixture of 200 ml of 80% aqueous methanol and 100 ml of ethanol and, then, with a mixture of 200 ml of 80% aqueous ethanol and 200 ml of ether. It was then lyophilized to recover 2.0 g of CMTAK. Carboxymethyl content: 1.07.

EXAMPLE 16

In 33 ml of water was suspended 3.2 g of TAK-N ($\overline{DP}$ 255) and, under stirring at room temperature, 1 g of sodium hydroxide was added, followed by addition of 2.4 g of sodium monochloroacetate. The carboxymethylation reaction was thus conducted at room temperature with constant stirring for 2 hours. Thereafter, 1 g of sodium hydroxide and 2.4 g of sodium monochloroacetate were added again and the reaction was further conducted at room temperature with stirring for 3 hours. Then, 1 g of sodium hydroxide and 2.4 g of sodium monochloroacetate were further added. The reaction was continued at room temperature with stirring for an additional 2 hours. To the reaction mixture was added 1 liter of ethanol and the resulting precipitate was washed well with ethanol on a glass filter until the filtrate ceased to give a red color with phenolphthalein. It was then dried at 50° C. and under reduced pressure. The resulting powder (3.7 g) was dissolved in 90 ml of water and neutralized with acetic acid, followed by addition of 210 ml of ethanol. The resulting precipitate was collected by centrifugation, washed with 80% aqueous ethanol and lyophilized. By the above procedure was obtained 2.6 g of CMTAK. Carboxymethyl content: 0.30.

EXAMPLE 17

In 66 ml of water was suspended 6.4 g of TAK-N ($\overline{DP}$ 255) and, under ice-cooling and stirring, 4 g of sodium hydroxide and, then, 9.6 g of sodium monochloroacetate were added. The carboxymethylation was conducted under ice-cooling and stirring for 2 hours. Then, 4 g of sodium hydroxide and 9.6 g of sodium monochloroacetate were added again and the mixture was stirred under ice-cooling for 3 hours. Thereafter, 4 g of sodium hydroxide and 9.6 g of sodium monochloroacetate were further added and the reaction was continued under ice-cooling and stirring for 3 hours. To the reaction mixture was added 1 liter of ethanol and the resulting precipitate was washed well with ethanol on a glass filter until the filtrate ceased to give a red color with phenolphthalein, followed by drying at 50° C. and under reduced pressure. The resulting powder (8.6 g) was dissolved in 172 ml of water and neutralized with acetic acid. Then, following the addition of 480 ml of ethanol, the precipitate was collected by centrifugation, washed with 80% aqueous ethanol and lyophilized. By the above procedure was obtained 5.6 g of CMTAK. Carboxymethyl content: 0.36.

EXAMPLE 18

In 40 ml of isopropyl alcohol was suspended 1.5 g of TAK-D (F-I, $\overline{DP}$ 299) and the carboxymethylation was conducted as in Example 14. The product was washed as in Example 14 to obtain 1.9 g of CMTAK. Carboxymethyl content: 0.59.

The same TAK-D as above was suspended in 40 ml of isopropyl alcohol and, by the same procedure as that described in Example 15, the carboxymethylation was carried out. The reaction product was washed as in Example 15 to recover 2.2 g of CMTAK. Carboxymethyl content: 1.15.

EXAMPLE 19

In 40 ml of isopropyl alcohol was suspended 1.5 g of each of TAK-D(F-II, $\overline{DP}$ 113) and TAK-D(S-III, $\overline{DP}$ 68), respectively. And, as in Example 14, the carboxymethylation was carried out. The respective reaction products were collected by centrifugation, dissolved in 40 ml of water and neutralized with acetic acid. To each of these two neutral solutions was added 90 ml of methanol and the resulting precipitate was collected by centrifugation and washed well first with 200 ml of 80% aqueous methanol and then with 200 ml of aqueous ethanol, followed by lyophilizing. By the above procedure were obtained two species of CMTAK.

|  | Yield | Carboxymethyl content |
|---|---|---|
| CMTAK (obtained from F-II) | 1.4 g | 0.51 |
| CMTAK (obtained from S-III) | 1.4 g | 0.36 |

EXAMPLE 20

In 40 ml of isopropyl alcohol was suspended 1.5 g of each of TAK-D(F-II, $\overline{DP}$ 113) and TAK-D(S-III, $\overline{DP}$ 68) respectively and, as in Example 15, the carboxymethylation was carried out. The reaction products were washed respectively as in Example 19 to recover two species of CMTAK.

|  | Yield | Carboxymethyl content |
|---|---|---|
| CMTAK (obtained from F-II) | 2.3 g | 1.22 |
| CMTAK (obtained from S-III) | 1.4 g | 0.45 |

We claim:
1. A carboxymethylated $\beta$-1,3-glucan of the formula:

wherein at least one of the R's is —CH$_2$COOH, with the remainder being H; n is an integer, and pharmaceutically acceptable salts thereof, which is produced by carboxymethylating β-1,3-glucan or its hydrolysate shown by the formula wherein n is an integral number, and whose average degree of polymerization is between 2 and 1000.

2. The carboxymethylated β-1,3-glucan as claimed in claim 1, wherein the average degree of polymerization is between 15 and 800.

3. The carboxymethylated β-1,3-glucan as claimed in claim 2, wherein the average degree of polymerization is between 40 and 600.

4. The carboxymethylated β-1,3-glucan as claimed in claim 1, wherein the degree of substitution of the carboxymethyl groups is between 0.30 and 1.22.

5. The carboxymethylated β-1,3-glucan as claimed in claim 1, wherein said β-1,3-glucan is produced by a microorganism belonging to the genus Alcaligenes or the genus Agrobacterium and is water-insoluble and thermogelable in the presence of water at an average degree of polymerization of 170, and said hydrolysate is a lower polymer obtainable upon partial hydrolysis of said β-1,3-glucan.

6. The carboxymethylated β-1,3-glucan as claimed in claim 4, wherein the degree of substitution of the carboxymethyl groups is between 0.45 and 0.75.

* * * * *